(12) United States Patent
Kuo et al.

(10) Patent No.: US 10,345,301 B2
(45) Date of Patent: Jul. 9, 2019

(54) **METHOD FOR TREATING INFECTION OF GROUP A *STREPTOCOCCUS***

(71) Applicant: I-SHOU UNIVERSITY, Kaohsiung (TW)

(72) Inventors: Chih-Feng Kuo, Kaohsiung (TW); Ni-Na Tsao, Kaohsiung (TW); Ching-Chuan Liu, Kaohsiung (TW); Tzong-Shiann Ho, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 0 days.

(21) Appl. No.: 15/818,478

(22) Filed: Nov. 20, 2017

(65) Prior Publication Data

US 2019/0094220 A1 Mar. 28, 2019

(30) Foreign Application Priority Data

Sep. 28, 2017 (TW) .............................. 106133438 A

(51) Int. Cl.
*A61K 39/40* (2006.01)
*G01N 33/569* (2006.01)
*C07K 16/12* (2006.01)
*A61K 39/00* (2006.01)

(52) U.S. Cl.
CPC ... *G01N 33/56944* (2013.01); *C07K 16/1275* (2013.01); *A61K 2039/54* (2013.01); *G01N 2333/315* (2013.01); *G01N 2469/20* (2013.01)

(58) Field of Classification Search
None
See application file for complete search history.

(56) References Cited

PUBLICATIONS

Chih-Feng Kuo et al., "Immunization with a streptococcal multiple-epitope recombinant protein protests mice against invasive group A streptococcal infection", PLOS ONE, Mar. 29, 2017, vol. 12, p. 1-20, Brazil.
Bart J. M. Vlaminckx et al., "Site-Specific Manifestations of Invasive Group A Streptococcal Disease: Type Distribution and Corresponding Patterns of Virulence Determinants", Journal of Clinical Microbiology, Nov. 2003, vol. 41, p. 4941-4949, Germany.
NCBI Blast protein Sequence, search condition: amino acid (SEQ ID No. 10 abbreviation), database: All non-redundant Genbank CDS translations+PDB+SwissProt+PIR, program: Blast 2.8.0+, search time: Jun. 25, 2018.

*Primary Examiner* — Jana A Hines
*Assistant Examiner* — Khatol S Shahnan Shah
(74) *Attorney, Agent, or Firm* — WPAT, PC

(57) ABSTRACT

A method for treating infection of group A *Streptococcus* (GAS) includes grouping a patient infected with GAS into an invasive infected candidate. An antibiotic is then administrated to the invasive infected candidate to treat the infection of GAS. Moreover, the patient is grouped into the invasive infected candidate when a first detected level, determined by ex vivo contacting a first biopsy obtained from the patient with a FSBM recombinant protein having an amino acid sequence set forth as SEQ ID NO: 10, is smaller than 0.6.

5 Claims, 1 Drawing Sheet
Specification includes a Sequence Listing.

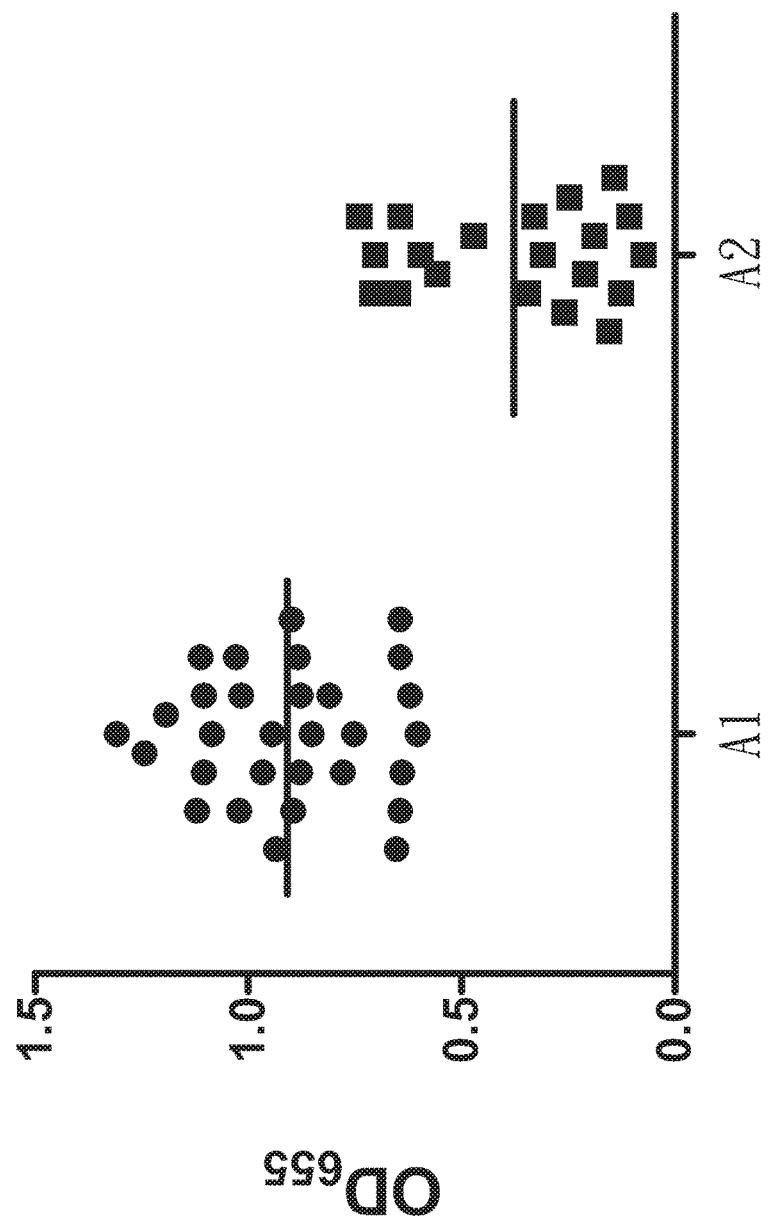

SEQUENCE LISTING

<160> NUMBER OF SEQ ID NOS: 10

<210> SEQ ID NO 1
<211> LENGTH: 114
<212> TYPE: DNA
<213> ORGANISM: Artificial Sequence
<220> FEATURE:
<223> OTHER INFORMATION: Nucleic acid sequence of the first DNA fragment
      being expressed as the peptide corresponding to the FnBR domain of
      Sfb1

<400> SEQUENCE: 1
agatctggta tgagtggaca aacaacacca caagtagaaa ctgaagacac caaggaaccc        60
ggggtgctga tgggcggcca gagcgagtct gttgaattca ctaaggatac ccag             114

<210> SEQ ID NO 2
<211> LENGTH: 63
<212> TYPE: DNA
<213> ORGANISM: Artificial Sequence
<220> FEATURE:
<223> OTHER INFORMATION: Nucleic acid sequence of the second DNA
      fragment being expressed as the peptide corresponding to the
      immunogenic domain of SLS

<400> SEQUENCE: 2
ttctcaattg ctaccgggtc tggaaattct caaggaggtt ctggatctta cacgccgggc        60

```
aag                                                                 63

<210> SEQ ID NO 3
<211> LENGTH: 69
<212> TYPE: DNA
<213> ORGANISM: Artificial Sequence
<220> FEATURE:
<223> OTHER INFORMATION: Nucleic acid sequence of the third DNA fragment
      being expressed as the peptide corresponding to the C3-binding
      motif of SPE B

<400> SEQUENCE: 3
gccctcggta caggcggtgg ggcaggaggg tttaacggct atcagtctgc cgtggtcgga      60
atcaagcct                                                             69

<210> SEQ ID NO 4
<211> LENGTH: 84
<212> TYPE: DNA
<213> ORGANISM: Artificial Sequence
<220> FEATURE:
<223> OTHER INFORMATION: Nucleic acid sequence of the fourth DNA
      fragment being expressed as the peptide corresponding to the
      C-terminal conserved segment of M protein

<400> SEQUENCE: 4
caggccgagg ataaagtgaa acaaagtagg gaggctaaga acaggtgga gaaggcattg       60 aagcagcttg aggacaaagt ccag                                            84

<210> SEQ ID NO 5
<211> LENGTH: 38
<212> TYPE: PRT
<213> ORGANISM: Artificial Sequence
<220> FEATURE:
<223> OTHER INFORMATION: Amino acid sequence of the first peptide
      fragment corresponding to the FnBR domain of Sfb1

<400> SEQUENCE: 5

Arg Ser Gly Met Ser Gly Gln Thr Thr Pro Gln Val Glu Thr Glu Asp
1               5                   10                  15

Thr Lys Glu Pro Gly Val Leu Met Gly Gly Gln Ser Glu Ser Val Glu
            20                  25                  30

Phe Thr Lys Asp Thr Gln
        35

<210> SEQ ID NO 6
<211> LENGTH: 21
<212> TYPE: PRT
<213> ORGANISM: Artificial Sequence
<220> FEATURE:
<223> OTHER INFORMATION: Amino acid sequence of the second peptide
      fragment corresponding to the immunogenic domain of SLS

<400> SEQUENCE: 6

Phe Ser Ile Ala Thr Gly Ser Gly Asn Ser Gln Gly Gly Ser Gly Ser
1               5                   10                  15

Tyr Thr Pro Gly Lys
            20

<210> SEQ ID NO 7
<211> LENGTH: 23
<212> TYPE: PRT
<213> ORGANISM: Artificial Sequence
<220> FEATURE:
<223> OTHER INFORMATION: Amino acid sequence of the third peptide
``` fragment corresponding to the C3-binding motif of SPE B

<400> SEQUENCE: 7

Ala Leu Gly Thr Gly Gly Gly Ala Gly Gly Phe Asn Gly Tyr Gln Ser
1               5                   10                  15

Ala Val Val Gly Ile Lys Pro
            20

<210> SEQ ID NO 8
<211> LENGTH: 28
<212> TYPE: PRT
<213> ORGANISM: Artificial Sequence
<220> FEATURE:
<223> OTHER INFORMATION: Amino acid sequence of the fourth peptide
      fragment corresponding to the C-terminal conserved segment of M
      protein

<400> SEQUENCE: 8

Gln Ala Glu Asp Lys Val Lys Gln Ser Arg Glu Ala Lys Lys Gln Val
1               5                   10                  15

Glu Lys Ala Leu Lys Gln Leu Glu Asp Lys Val Gln
            20                  25

<210> SEQ ID NO 9
<211> LENGTH: 357
<212> TYPE: DNA
<213> ORGANISM: Artificial Sequence
<220> FEATURE:
<223> OTHER INFORMATION: Nucleic acid sequence used to express as the
      FSBM recombinant protein according to present invention

<400> SEQUENCE: 9
agatctggta tgagtggaca acaacacca caagtagaaa ctgaagacac caaggaaccc      60
ggggtgctga tgggcggcca gagcgagtct gttgaattca ctaaggatac ccaggtcgac    120
ttctcaattg ctaccgggtc tggaaattct caaggaggtt ctggatctta cacgccgggc    180
aagtgcggta ccgccctcgg tacaggcggt ggggcaggag ggtttaacgg ctatcagtct    240
gccgtggtcg gaatcaagcc tggatcccag gccgaggata agtgaaaca aagtagggag     300 gctaagaaac aggtggagaa ggcattgaag cagcttgagg acaaagtcca gtctaga       357

<210> SEQ ID NO 10
<211> LENGTH: 119
<212> TYPE: PRT
<213> ORGANISM: Artificial Sequence
<220> FEATURE:
<223> OTHER INFORMATION: Amino acid sequence of the FSBM recombinant
      protein according to the present invention

<400> SEQUENCE: 10

Arg Ser Gly Met Ser Gly Gln Thr Thr Pro Gln Val Glu Thr Glu Asp
1               5                   10                  15

Thr Lys Glu Pro Gly Val Leu Met Gly Gly Gln Ser Glu Ser Val Glu
            20                  25                  30

Phe Thr Lys Asp Thr Gln Val Asp Phe Ser Ile Ala Thr Gly Ser Gly
        35                  40                  45

Asn Ser Gln Gly Gly Ser Gly Ser Tyr Thr Pro Gly Lys Cys Gly Thr
    50                  55                  60

Ala Leu Gly Thr Gly Gly Gly Ala Gly Gly Phe Asn Gly Tyr Gln Ser
65                  70                  75                  80

Ala Val Val Gly Ile Lys Pro Gly Ser Gln Ala Glu Asp Lys Val Lys
                85                  90                  95

```
Gln Ser Arg Glu Ala Lys Lys Gln Val Glu Lys Ala Leu Lys Gln Leu
            100                 105                 110
Glu Asp Lys Val Gln Ser Arg
            115
```

METHOD FOR TREATING INFECTION OF GROUP A *STREPTOCOCCUS*

CROSS REFERENCE TO RELATED APPLICATIONS

The application claims the benefit of Taiwan application serial No. 106133438, filed on Sep. 28, 2017, and the entire contents of which are incorporated herein by reference.

BACKGROUND OF THE INVENTION

1. Field of the Invention

The present invention relates to a method for treating infection of group A *Streptococcus* (GAS) and, more particularly, to a method for treating the infection of GAS including grouping a patient into an invasive infected candidate using a FSBM recombinant protein.

2. Description of the Related Art

*Streptococcus*, which is belonging to the phylum Firmicutes, is a genus of coccus (spherical) Gram-positive bacteria. Bacteria belonging to this genus divide alone with single axis which lead them to grow in pairs or chains, and therefore are named as *Streptococcus*.

Species of *Streptococcus* can be further categorized by their hemolytic property. The majority among them is group A *Streptococcus* (GAS). At early stage, infection of GAS leads to symptoms similar to common cold such as fever, sore throat or rash. Nonetheless, the infection of GAS without proper treatment will lead to severe diseases such as scarlet fever, pharyngitis, necrotizing fasciitis, streptococcal toxic shock symptoms (STSS) or cellulitis and cause more than 500,000 deaths per year.

The infection of GAS can be diagnosed by conventional methods such as rapid antigen detection and throat culture. However, by the conventional methods, the patients infected with GAS cannot be grouped into an invasive infected group, who have a tendency of having severe symptoms like necrotizing fasciitis, STSS or cellulitis, etc., and into a noninvasive infected group, who only have mild symptoms like scarlet fever or pharyngitis. Thus, physicians are not able to use limited medical resources to treating invasive infected patients who are grouped into the invasive infected group. This not only results in a waste of the limited medical resource, but more importantly, the invasive infected patients the golden hour to treat the invasive infected patients is probably missed.

In light of this, there is a need in the art for a method for treating the infection of GAS.

SUMMARY OF THE INVENTION

It is therefore the objective of the present invention to provide a method for treating infection of group A *Streptococcus* (GAS).

One embodiment of the invention discloses a method for treating the infection of GAS. The method for treating the infection of GAS includes: grouping a patient infected with GAS into an invasive infected candidate. An antibiotic is administrated to the invasive infected candidate to treat the infection of GAS. Moreover, the patient is grouped into the invasive infected candidate when the first detected level is smaller than 0.6. The first detected level is determined by ex vivo contacting a first biopsy obtained from the patient with a FSBM recombinant protein having an amino acid sequence set forth as SEQ ID NO: 10. Accordingly, the method for treating the infection of GAS according to the present invention can effectively group the patients infected with GAS into the invasive infected candidates who have the tendency of having sever symptoms. Therefore, physicians can use the limited medical resource to treat the invasive infected candidates. With such performance, a waste of the limited medical resource can be decreased, and the invasive infected candidates can be treated in the golden hour to reduce the risk of death the invasive infected candidates.

In an example, the patient is grouped into the invasive infected candidate when a difference between a second detected level and the first detected level is smaller than 0.3. The second detected level is determined by ex vivo contacting a second biopsy with the FSBM protein. The second biopsy is obtained from the patient 4-10 days later after obtaining the first biopsy from the patient. Moreover, intravenous immunoglobin G (IVIG) is administrated to the invasive infected candidate when the difference between the second detected level and the first detected level is smaller than 0.3. Accordingly, the patient can be more effectively grouped into the invasive infected candidate, and can be more effectively treated.

In an example, the first biopsy is selected from a serum biopsy or a plasma biopsy, and the second biopsy is selected from a serum biopsy or a plasma biopsy.

In an example, a first complex is formed by the FSBM protein and an antibody against the FSBM recombinant protein in the first biopsy. A formation level of the first complex is detected as the first detected level. As an example, a second antibody is used to combine with the first complex, and an absorbance at 655 nm of the second antibody combined with the first complex is detected as the first detected level. Moreover, a second complex is formed by the FSBM protein and an antibody against the FSBM recombinant protein in the second biopsy. A formation level of the second complex is detected as the second detected level. As an example, a second antibody is used to combine with the second complex, and an absorbance at 655 nm of the second antibody combined with the second complex is detected as the second detected level.

BRIEF DESCRIPTION OF THE DRAWINGS

The present invention will become more fully understood from the detailed description given hereinafter and the accompanying drawing which is given by way of illustration only, and thus is not limitative of the present invention, and wherein:

The SOLE FIGURE is a scatter plot illustrating distributions of first detected level of biopsy obtained from patients of groups A1 and A2.

DETAILED DESCRIPTION OF THE INVENTION

A method for treating infection of group A *streptococcus* (GAS) according to an embodiment of the present invention includes obtaining a biopsy from a patient. A detected level is determined by ex vivo contacting the biopsy with a FSBM recombinant protein. The detected level can be then used to evaluate if the patient is an invasive infected candidate who has a tendency of having severe symptoms like necrotizing fasciitis, STSS or cellulitis, etc.). Moreover, a therapeutically effective amount of a medicament can be administrated to the invasive infected candidate.

In detail description, the patient is a subject infected with GAS. The biopsy can be selected, but not to be limited, from a serum biopsy or a plasma biopsy, which can be appreciated by a person having ordinary skill in the art.

The FSBM recombinant protein according to the present invention can include a first peptide fragment, a second peptide fragment, a third peptide fragment and a fourth peptide fragment. The first peptide fragment is derived from a partial fragment of the FnBR domain of Sfb1 (one of the fibronectin-binding proteins), the second peptide fragment is derived from a partial fragment of the immunogenic domain of SLS (streptolysin S), the third peptide fragment is derived from a partial fragment of the C3-binding motif of SPE B (streptococcal pyrogenic exotoxin B), and the fourth peptide fragment is derived from a partial fragment of the C-terminal conserved segment of M protein.

The FSBM recombinant protein can be expressed by $E.\ coli$ cells. As an example, an expression plasmid for expressing the FSBM recombinant protein can be constructed and transformed into the $E.\ coli$ cells. The FSBM recombinant protein expressed by the $E.\ coli$ cells can be purified, and the purified FSBM recombinant protein can therefore be obtained.

Specifically, the expression plasmid comprises a first DNA fragment corresponding to the first peptide fragment, a second DNA fragment corresponding to the second peptide fragment, a third DNA fragment corresponding to the third peptide fragment and a fourth DNA fragment corresponding to the fourth peptide fragment. Moreover, the first, second, third and fourth DNA fragments preferably have the codon usage of $E.\ coli$, thus the $E.\ coli$ cells can show preferable expression efficiency.

In this embodiment, the first, second, third and fourth DNA fragments have nucleic acid sequences set forth as SEQ ID NOS: 1, 2, 3 and 4, respectively. In addition, the first, second, third and fourth peptide fragments expressed by the $E.\ coli$ cells have the amino acid sequences set forth as SEQ ID NOS: 5, 6, 7 and 8, respectively.

Furthermore, a linker fragment can be added between the first and second DNA fragments, the second and third DNA fragments, and the third and fourth DNA fragments. The sequence of the linker fragment can be appreciated by a person having ordinary skill in the art. Therefore, detail description is not given to avoid redundancy. In this embodiment, the expression plasmid comprises a nucleic acid sequence set forth as SEQ ID NO: 9, while the FSBM recombinant protein expressed by the $E.\ coli$ cells has an amino acid sequence set forth as SEQ ID NO: 10.

The construction of the expression plasmid is well known in the field and is therefore not limited to the following statement. In this embodiment, the DNA fragment with the nucleic acid sequence set forth as SEQ ID NO: 9 is synthesized and digested by the restriction enzyme. The digested DNA fragment is then ligated to a pET-24a vector by a ligase, and the expression plasmid is obtained.

In this embodiment, after the expression plasmid is transformed into the $E.\ coli$ BL21(DE) pLysS, the $E.\ coli$ BL21(DE) pLysS can express the fusion protein with 6×His tag by IPTG induction. The FSBM recombinant protein can be then purified using $Ni^{2+}$ chelating chromatography.

The above-mentioned purified FSBM recombinant protein can be used to contact with the biopsy to determine the detected level. For instance, a complex can be formed by the FSBM recombinant protein and an antibody against the FSBM recombinant protein in the biopsy, and the formation level of the complex (the FSBM-antibody complex) can be detected as the detected level. The way to determine the detected level includes, but not to be limited to, Western blotting, immunoprecipitation assay, enzyme-linked immunosorbent assay (ELISA), immunofluorescence assay, immunodiffusion assay, immunoelectrophorsis assay and magnetic immunoassay, which can be appreciated by a person having ordinary skill in the art.

In this embodiment, the FSBM recombinant protein is coated on a 96-well plate. The biopsy can then be added to the 96-well plate, and the FSBM-antibody complex can be formed by the FSBM recombinant protein and the antibody against the FSBM recombinant protein in the biopsy. Furthermore, a second antibody is used to combine with the FSBM-antibody complex to form another complex (that is, a FSBM-antibody-$2^{nd}$ antibody complex). The FSBM-antibody-$2^{nd}$ antibody complex has a maximum absorbance at 655 nm. Therefore, the detected level can be determined by detecting the absorbance of the FSBM-antibody-$2^{nd}$ antibody complex at 655 nm.

It is worth noting that, physicians can collect the biopsy (that is, a first biopsy) from the patient and can contact the biopsy with the FSBM recombinant protein to determine the detected level (that is, a first detected level). The patient infected with GAS can be grouped into an invasive infected candidate when the first detected level is lower than a threshold. In this embodiment, the patient can be grouped into an invasive infected candidate when the detecting level is lower than 0.6. Therefore, physicians can effectively evaluate if the patient belongs to the invasive infected candidate who has a tendency of having severe symptoms like necrotizing fasciitis, STSS or cellulitis etc., and further use limited medical resources to treat the patient. For instance, physicians can treat the patient by co-administrating clindamycin and penicillin, or co-administrating clindamycin and β-lactamase inhibitors such asticarcillin-clavulanate and piperacillin-tazobactam, or co-administrating clindamycin and carbapenem such as meropenem or imipenem, or co-administrating clindamycin and vancomycin, or co-administrating clindamycin and daptomycin.

Moreover, in order to enhance the accuracy of grouping the patient into an invasive infected candidate, in the second embodiment, when the first detected level is smaller than 0.6, physicians can obtain another biopsy (that is, a second biopsy) 4 to 10 days later after obtaining the first biopsy, and a second detected level can be determined by the same detecting process described above. The patient can be grouped into the invasive infected candidate when the difference between the second detected level and the first detected level (i.e., the second detected level minus the first detected level) is lower than 0.3. Besides, the patient can also be considered who has bad immune responses to virulence factors of GAS such as Sfb1, SLS, SPE B and M protein.

By the method for treating the infection of GAS according to the second embodiment of the present invention, the patient can not only to be grouped into the invasive infected candidate more effectively, but more importantly, can further be administered by intravenous immunoglobin G (IVIG), improving the treating effect.

To validate the method for treating the infection of GAS according to the first and the second embodiments of the present invention can be used to effectively treat the patients infected with GAS, the following trials are carried out.

Fifty patients infected with GAS are used in this trial. Only twenty of them are grouped into the invasive infected candidates (group A2), in which twelve of them have necrotizing fasciitis and eight of them have cellulitis. Moreover, thirty of the fifty patients (group A1) include eighteen patients with scarlet fever and twelve patients with pharyngitis. When the patients are hospitalized, serum biopsies are collected as the first biopsies from the patients, and the corresponding first detected level of the serum biopsies is determined. The distributions of the first detected level of the serum biopsies obtained from the patients of group A1 and A2 are shown in the SOLE FIGURE. The mean value of the first detected level of the serum biopsies obtained from the patients of group A1 is 0.9088±0.03669, and the mean value of the first detected level of the serum biopsies obtained from the patients of group A2 is 0.3785±0.05172, suggesting that the method for treating the infection of GAS according to the first embodiment of the present invention can effectively group the patients infected with GAS into the invasive infected candidates. Thus, physicians can use the limited medical resources to treat the invasive infected candidates who have the tendency of having severe symptoms.

Moreover, 4-10 days later after the patients of group A2 are hospitalized, serum biopsies are collected as the second biopsies from the patients of group A2, and the corresponding second detected level of the serum biopsies is determined. The differences between the second detected level and the first detected level (i.e., the second detected level minus the first detected level) of group A2 are shown in Table 1.

TABLE 1

| No. of subjects | First detected level | Second detected level | Differences between the second and the first detected level |
|---|---|---|---|
| #01 | 0.0900 | 0.1925 | 0.1025 |
| #02 | 0.3140 | 0.2365 | −0.0775 |
| #03 | 0.3245 | 0.4460 | 0.1215 |
| #04 | 0.3610 | 0.6055 | 0.2445 |
| #05 | 0.3465 | 0.3620 | 0.0115 |
| #06 | 0.3835 | 0.6165 | 0.2330 |

TABLE 1-continued

| No. of subjects | First detected level | Second detected level | Differences between the second and the first detected level |
|---|---|---|---|
| #07 | 0.3940 | 0.4970 | 0.1030 |
| #08 | 0.4150 | 0.4670 | 0.0520 |
| #09 | 0.4525 | 0.5550 | 0.1025 |
| #10 | 0.4525 | 0.3950 | −0.0575 |
| #11 | 0.5440 | 0.4550 | −0.0890 |
| #12 | 0.5480 | 0.4225 | −0.1255 |

Referring to Table 1, the differences between the second detected level and the first detected level in the twelve patients tested are smaller than 0.3, indicating that the method for treating the infection of GAS according to the second embodiment of the present invention can effectively group the patients infected with GAS into the invasive infected candidates. Thus, physicians can use the limited medical resources to treat the invasive infected candidates who have the tendency of having severe symptoms.

Accordingly, the method for treating the infection of GAS according to the present invention can effectively group the patients infected with GAS into the invasive infected candidates who have the tendency of having sever symptoms. Therefore, physicians can use the limited medical resources to treat the invasive infected candidates. With such performance, a waste of the limited medical resources can be decreased, and the invasive infected candidates can be treated in the golden hour to reduce the risk of death the invasive infected candidates.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for treating infection of group A *Streptococcus* (GAS), comprising:
   grouping a patient infected with GAS into an invasive infected candidate; and
   administrating an antibiotic to the invasive infected candidate to treat the infection of GAS,
   wherein grouping the patient into the invasive infected candidate including:
      obtaining a first biopsy from the patient;
      ex vivo contacting the first biopsy with a FSBM recombinant protein having an amino acid sequence set forth as SEQ ID NO: 10 to form a first complex by the FSBM recombinant protein and an antibody against the FSBM recombinant protein in the first biopsy;
      combining the first complex with a second antibody; and
      determining a first detected level by detecting an absorbance at 655 nm of the second antibody combined with the first complex;
      wherein the patient is grouped into the invasive infected candidate when the first detected level is smaller than 0.6.

2. The method for treating the infection of GAS as claimed in claim 1, wherein grouping the patient into the invasive infected candidate further including:
   obtaining a second biopsy from the patient 4-10 days later after obtaining the first biopsy from the patient; and
   ex vivo contacting the second biopsy with the FSBM recombinant protein to form a second complex by the FSBM recombinant protein and the antibody against the FSBM recombinant protein in the second biopsy;
   combining the second complex with the second antibody; and
   determining a second detected level by detecting an absorbance at 655 nm of the second antibody combined with the second complex;
   wherein the patient is grouped into the invasive infected candidate when the second detected level minus the first detected level is smaller than 0.3.

3. The method for treating the infection of GAS as claimed in claim 2, wherein the method for treating the infection of GAS further includes administrating intravenous immunoglobin G (IVIG) to the invasive infected candidate when the difference is smaller than 0.3.

4. The method for treating the infection of GAS as claimed in claim 1, wherein the first biopsy is selected from a serum biopsy or a plasma biopsy.

5. The method for treating the infection of GAS as claimed in claim 2, wherein the second biopsy is selected from a serum biopsy or a plasma biopsy.

* * * * *